United States Patent [19]

Green

[11] Patent Number: 4,520,817
[45] Date of Patent: Jun. 4, 1985

[54] SURGICAL INSTRUMENTS

[75] Inventor: David T. Green, Norwalk, Conn.

[73] Assignee: United States Surgical Corporation, Norwalk, Conn.

[21] Appl. No.: 356,247

[22] Filed: Mar. 8, 1982

Related U.S. Application Data

[63] Continuation-in-part of Ser. No. 118,664, Feb. 5, 1980, abandoned.

[51] Int. Cl.³ .................. A61B 17/04; A61B 17/11
[52] U.S. Cl. .................. 128/305; 128/334 R; 227/19; 227/76; 227/DIG. 1; 206/339
[58] Field of Search .................. 128/334 R, 346, 305, 128/321; 30/124; 83/385, 386, 455; 227/DIG. 1, 19, 135; 206/339; 227/76

[56] References Cited

U.S. PATENT DOCUMENTS

| | | | |
|---|---|---|---|
| 2,214,870 | 9/1940 | West | 83/455 |
| 3,078,465 | 2/1963 | Bobrov | 128/334 R |
| 3,079,606 | 3/1963 | Bobrov et al. | 128/334 R |
| 3,080,564 | 3/1963 | Strekopitov et al. | 227/153 |
| 3,137,192 | 6/1964 | McNeill | 83/455 |
| 3,252,643 | 5/1966 | Strekopytov et al. | 227/109 |
| 3,275,211 | 9/1966 | Hirsch et al. | 227/124 |
| 3,315,863 | 4/1967 | O'Dea | 227/19 |
| 3,317,105 | 5/1967 | Astafjev et al. | 227/76 |
| 3,490,675 | 1/1970 | Green et al. | 227/19 |
| 3,494,533 | 2/1970 | Green et al. | 227/19 |
| 3,499,591 | 3/1970 | Green | 227/76 |
| 4,060,089 | 11/1977 | Noiles | 128/325 |
| 4,207,898 | 6/1980 | Becht | 128/334 R X |
| 4,210,043 | 7/1980 | Urion et al. | 83/455 X |
| 4,241,861 | 12/1980 | Fleischer | 227/135 |

FOREIGN PATENT DOCUMENTS

| | | | |
|---|---|---|---|
| 869527 | 1/1953 | Fed. Rep. of Germany | 128/334 R |
| 7909218 | 8/1979 | Fed. Rep. of Germany | 128/334 R |
| 1278616 | 11/1961 | France | 128/334 R |
| 2310117 | 3/1975 | France | |
| 375481 | 4/1964 | Switzerland | 128/334 R |
| 1158111 | 7/1969 | United Kingdom | 128/334 R |
| 1158113 | 7/1969 | United Kingdom | 128/334 R |

Primary Examiner—Michael H. Thaler
Attorney, Agent, or Firm—John E. Nathan; Robert R. Jackson; Richard A. Inz

[57] ABSTRACT

A surgical stapling instrument is disclosed, having upper and lower elongate jaws, one of which is adapted to receive a staple magazine, the other jaw being adapted to receive an anvil or to serve as one itself. A pusher bar and knife assembly including a pair of pusher bars and a central knife carrier moves along the jaws to eject staples from the magazine sequentially and to form laterally spaced staple rows in tissue gripped between the jaws while the knife cuts the tissue along a line between the staple rows. The instrument includes structure for locally supporting the jaws in the region of the forward ends of the pusher bars as these elements move along the jaws to resist forces which arise during staple ejection and shaping and which tend to vertically separate or laterally distort the jaws, or both. The magazine and the pusher bar and knife assembly may together constitute a unitary disposable cartridge. One jaw may have tabs or lugs for gripping the other jaw to provide additional lateral stability. A detent may also be provided to prevent operation of the instrument while the jaws are open.

4 Claims, 25 Drawing Figures

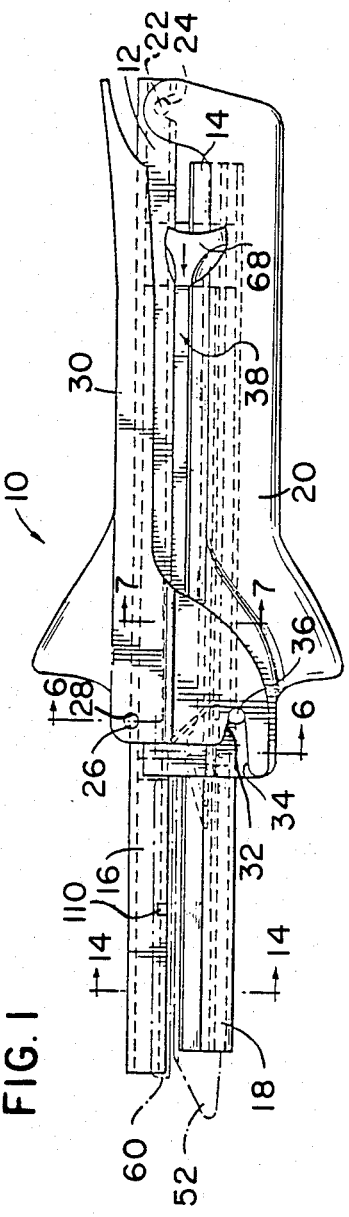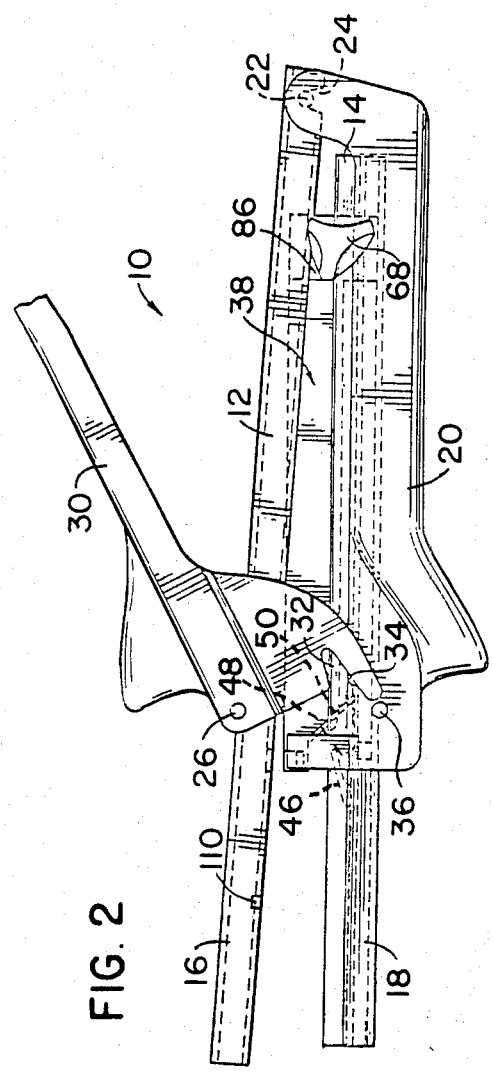
FIG. 1
FIG. 2

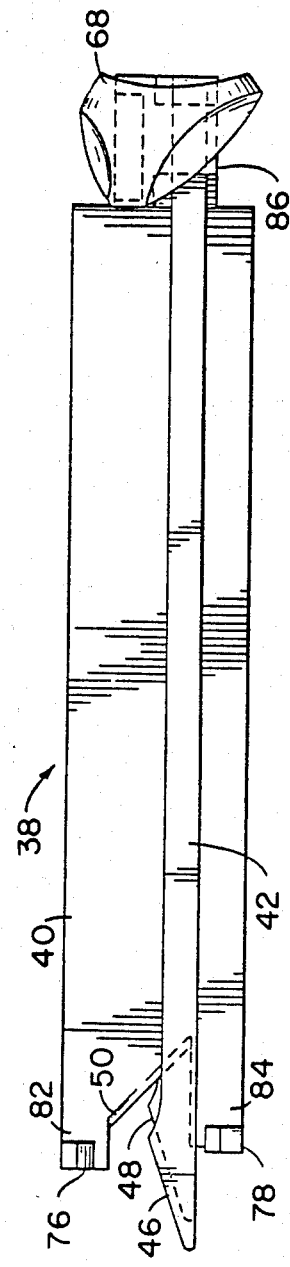
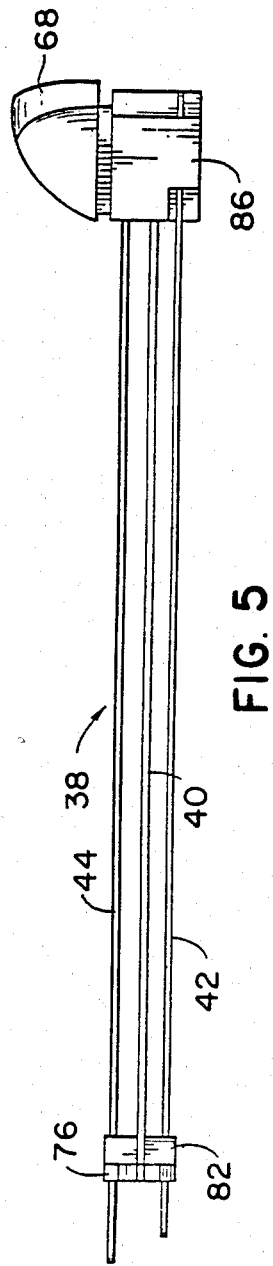
FIG. 4
FIG. 5

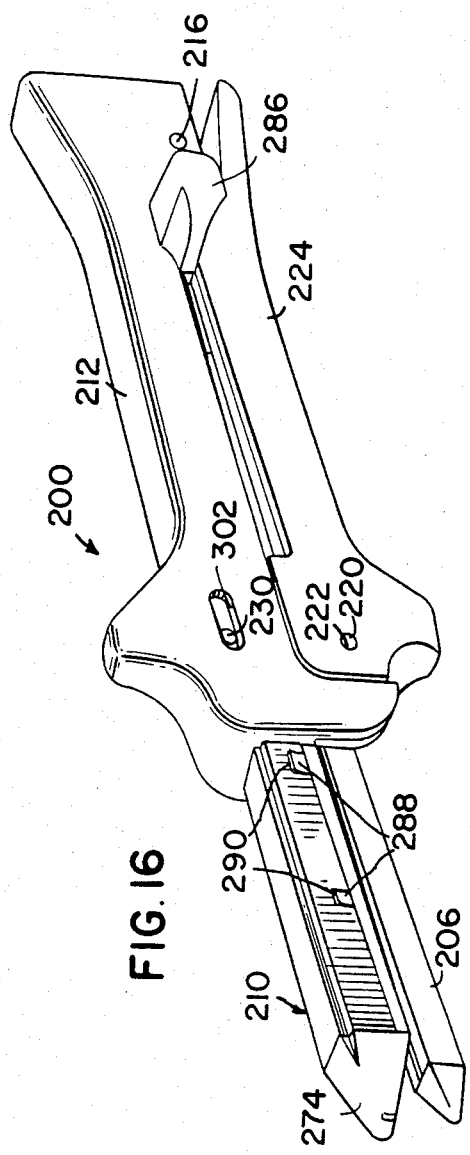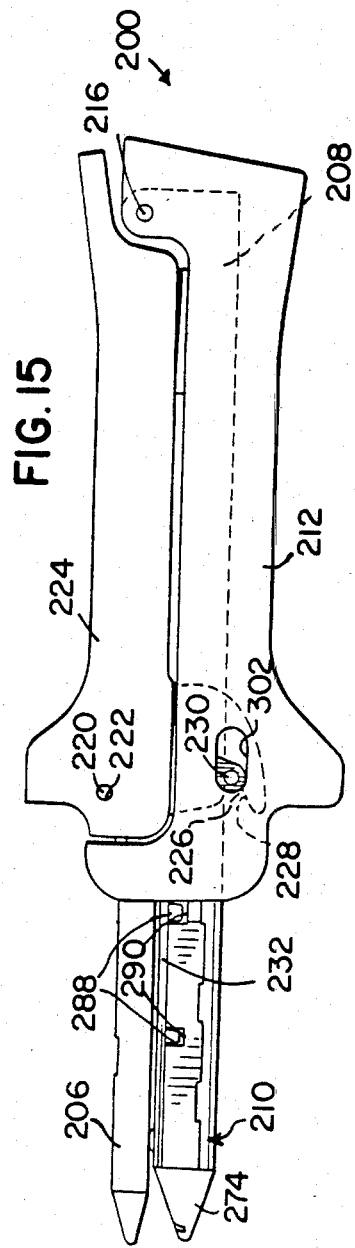

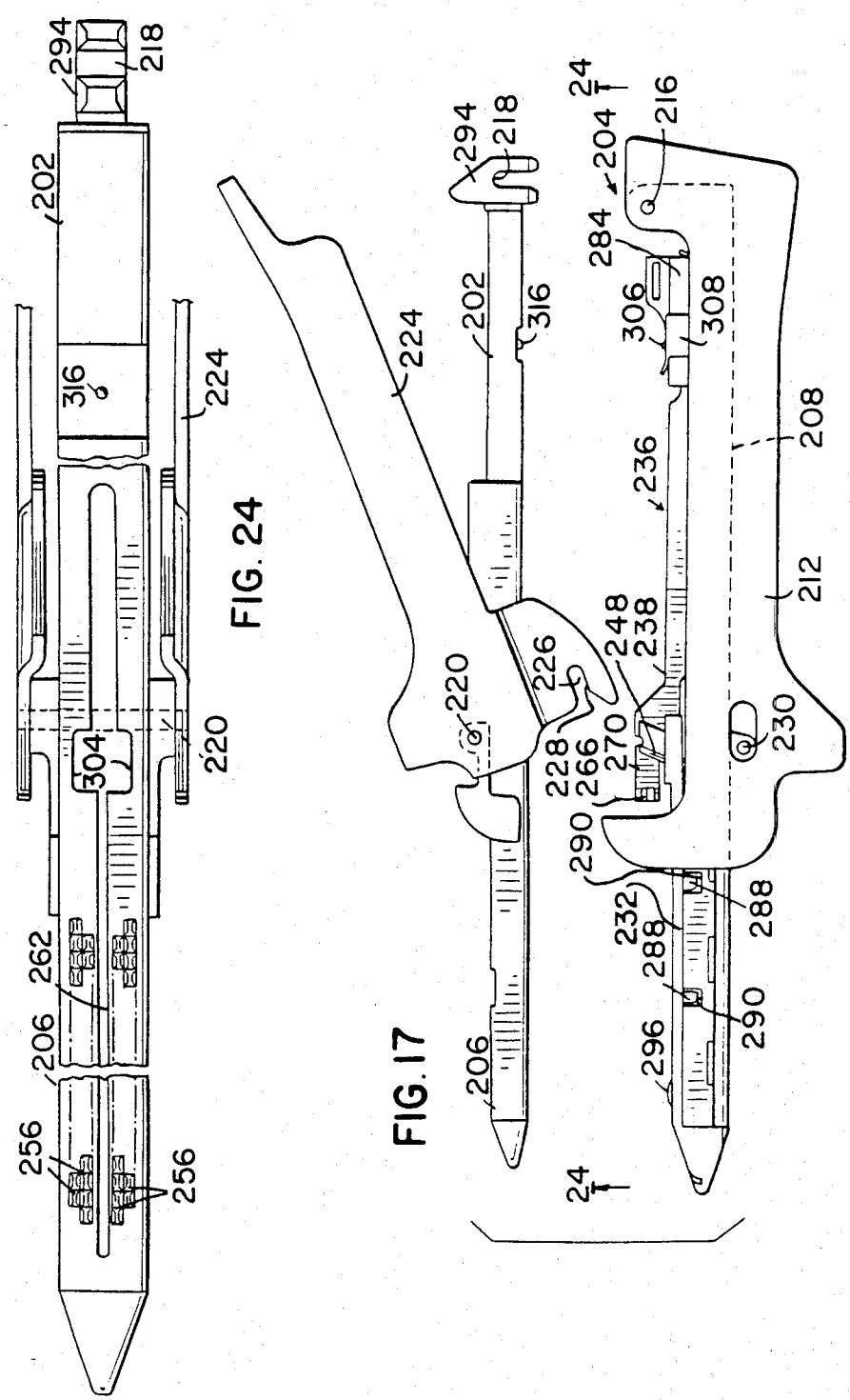

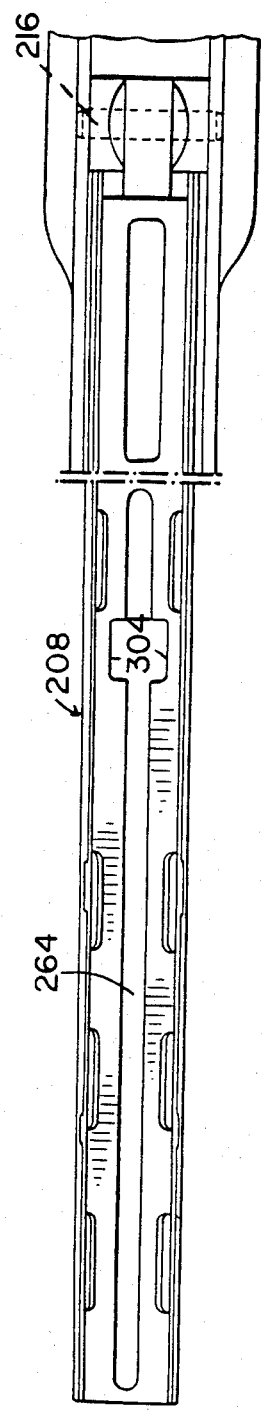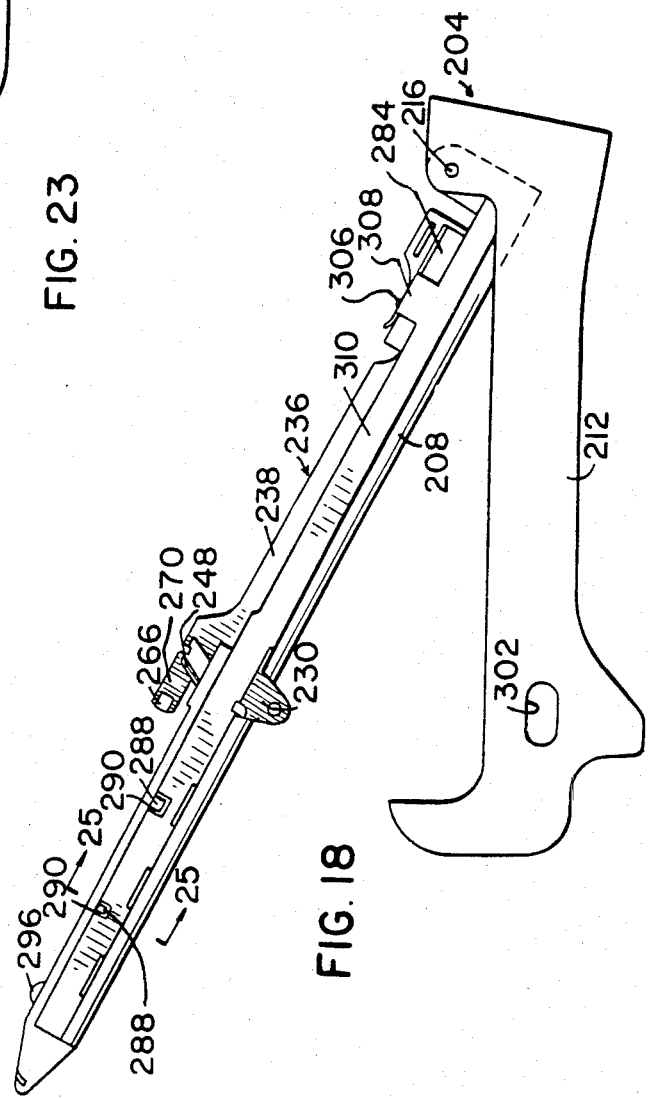
FIG. 23
FIG. 18

SURGICAL INSTRUMENTS

RELATED APPLICATIONS

This application is a continuation-in-part of the present inventor's copending application Ser. No. 118,664, filed Feb. 5, 1980, for IMPROVEMENTS IN SURGICAL INSTRUMENTS, now abandoned, assigned in common with the present application. The disclosure of application Ser. No. 118,664 is incorporated herein by reference.

BACKGROUND OF THE INVENTION

This invention relates to an instrument for use in applying surgical fasteners such as staples, clips and the like to living tissue. More particularly, the invention relates to a surgical stapling instrument for use in forming a plurality of laterally spaced rows of staples in an internal body organ. Typically, such an instrument comprises a pair of cooperating elongate jaw members. In use, one jaw member carries a staple cartridge with at least two laterally spaced rows of staples, and the other carries an anvil with staple-closing depressions aligned with the rows of staples in the cartridge. In the type of instrument to which the invention pertains, a pusher bar assembly is moved longitudinally along the jaws to eject staples from the cartridge sequentially by means of a camming action effected by cooperation of the forward end of the pusher bars with staple pushers carried by the cartridge in association with the individual staples. The camming action closes the staples against the anvil, forming laterally spaced lines of staples in tissue gripped between the jaws trailing the pusher bars.

In instruments of this kind, a knife is often associated with the pusher bars in such a manner as to move forward along the jaws in tandem with, but slightly behind, the pusher bars. As the pusher bar and knife assembly is moved forward, the knife cuts the tissue along a line between the staple rows. By way of example, one instrument of this type is disclosed in U.S. Pat. No. 3,499,591, commonly assigned herewith, the disclosure of which is incorporated herein by reference. (The discussion hereinafter of surgical staplers refers consistently to a "pusher bar and knife assembly", but, except for references to cutting of the tissue, is uniformly applicable to a stapler having no knife.)

The staple cartridges, anvils and pusher bar and knife assemblies have commonly been made of disposable plastics and low cost metal stampings, while the frames have more generally been constructed for repeated use and must be resterilized before each reuse. A surgical stapler must be cleaned and sterilized with great care to ensure that every portion of the instrument has been made aseptic, and hospital sterilization of such an instrument is a difficult and painstaking procedure.

In recent years, in order to obviate the need for repeated sterilization of instruments, the tendency in the surgical field has been toward the introduction of fully self-contained disposable instruments which are used for only a single operation and then discarded. Obviously, economics is a factor in the design of such disposable instruments, and it is desirable to design such instruments to use the lightest possible readily available, economical materials and to employ the most economical possible production techniques.

With stapling instruments of the type described, relatively large forces are involved in clamping the tissue to be fastened and in ejecting the individual staples, forcing them through the gripped tissue and closing them against the anvil. Such forces tend both to separate the jaws vertically and to distort the jaws laterally, thereby hindering accurate stapling. Although in instruments of heavy materials like steel this problem does not make the instrument either unreliable or difficult to use, this problem is of somewhat greater significance when lightweight, disposable materials are used for the manufacture of the jaw frames.

SUMMARY OF THE INVENTION

It is an object of the present invention to provide an instrument of the type described for applying surgical fasteners, in which the jaws are maintained in proper alignment and hold the tissue firmly and securely, without separation of the jaws, during application of the fasteners.

Another object of the invention is to provide a novel instrument for use in applying surgical fasteners to living tissue and particularly suited to use in surgical stapling procedures.

It is a further object of the invention to provide a surgical stapling or like fastening instrument having a design which allows the instrument to be manufactured in the main from relatively light weight, disposable materials while still providing proper alignment and stabilizing the jaws during stapling.

It is still another object of the invention to provide a surgical stapler which cannot accidentally be actuated before the tissue to be stapled is correctly located between and firmly gripped by the jaws.

It is yet another object of the invention to provide a reusable surgical stapler and a disposable loading unit therefor that can be assembled quickly, easily and reliably.

In accordance with the invention, the elongate jaws of a surgical stapling instrument of the kind described are provided with special support means that support the jaws during stapling, preferably near or at the point where the maximum jaw-deflecting forces occur. In the preferred embodiments, this is done by means of a support member which moves along the jaws with the pusher bar and knife assembly, although static support means for the jaws can be used also.

In one preferred embodiment, the pusher bar and knife assembly carries upper and lower support shoes or blocks which are rigidly connected and are accurately aligned with one another laterally. Each shoe fits closely, but slidably, in a respective passageway provided in a respective one of the jaws when the jaws are closed and travels along its passageway with the pusher bar and knife blade assembly when the latter is pushed forward to operate the stapler.

The shoes are located on a rigid portion of the pusher bar and knife assembly in the region of the pusher bar cams and the knife blade. The shoes are so shaped as to resist relative motion of the jaws in the region of the pusher bar cams as the cams progress along the jaws, resisting vertical jaw-opening forces during staple formation and tending to keep the jaws properly aligned and free of distortion. The support is concentrated in the region of each staple in turn as the pusher bar and knife assembly is moved along the jaws.

According to the most preferred embodiment, the jaw passageways are formed near the top surface of the bottom jaw and the lower surface of the top jaw, respectively, and each passageway communicates with the exterior of the stapler via a respective longitudinal slot extending along the length of the surface of the respective jaw. In this embodiment, the shoes are carried on upper and lower extensions of the portion of the pusher bar and knife assembly carrying the knife. The staple cartridge and the anvil, which are supported on the inner facing surfaces of the respective jaws, each comprise two respective laterally spaced elongate members. During stapling, the knife carrier extensions move along the longitudinal spaces defined between the respective elongate members.

By utilizing the shoes to support the jaws locally in the region of the pusher bar cams and the knife blade as these elements ride along the jaws, the effects of the jaw-opening forces are substantially minimized. The jaws themselves can therefore be made of light-weight construction, so that an instrument designed in accordance with the invention lends itself to manufacture in light-weight, inexpensive materials suitable for use in a disposable instrument.

According to a further aspect of the invention, the distal end of one jaw of the stapler is provided with two parallel lugs or tabs that project toward the other jaw and engage the lateral surfaces of the latter jaw between them when the jaws are closed. The tabs prevent relative lateral motion of the jaws altogether, thus stabilizing the jaws. (When tissue is gripped between the distal end of the jaws, the tissue prevents the tabs from actually engaging the other jaw, but it has been found that the tabs have substantially the same stabilizing effect whether tissue is gripped between the jaws or not.)

In order to prevent accidental operation of the stapler of the invention, a detent mechanism is provided. The detent mechanism comprises first and second detent elements that cooperate to lock the pusher bar and knife assembly in the rearward, or retracted, position, and a release mechanism for allowing the pusher bar and knife assembly to be moved when the jaws are closed. In one preferred embodiment, the first detent element is a peg located on the pusher bar and knife assembly, and the second detent element is a member which is immovable relative to the staple magazine and in which is defined a recess or aperture to receive the peg to prevent motion of the pusher bar and knife assembly relative to the magazine. The release mechanism is a second peg, located on the portion of the stapler frame bearing the other jaw. The second peg is so shaped and located that when the jaws are closed, the second peg presses the pusher bar and knife assembly in such a direction as to disengage the first peg from the recess or aperture. This arrangement makes it very difficult for the pusher bar and knife assembly to be pushed forward before the jaws have been closed and locked together over the tissue to be stapled.

Also according to the invention, a unitary disposable cartridge or loading unit, comprising a staple holder or magazine, pusher bar cams and a pusher bar and knife assembly, is used with a reusable surgical stapler body including a handle, two jaws, a preferably non-detachable anvil and means for locking the jaws to grip a layer of tissue between them.

These and other features and advantages of the invention will be more fully understood from the following detailed description of several preferred embodiments thereof, considered together with the accompanying figures, in which like reference characters refer to like elements throughout.

BRIEF DESCRIPTION OF THE FIGURES

FIG. 1 is a side view of one preferred embodiment of a surgical stapling instrument according to the invention, with the jaws closed;

FIG. 2 is a side view of the instrument of FIG. 1 with the jaws open;

FIG. 4 is a side view of the pusher bar and knfe assembly of the instrument of FIG. 1;

FIG. 5 is an underside plan view of the pusher bar and knife assembly of FIG. 1;

FIG. 15 is a side view of a second preferred embodiment of a surgical stapling instrument according to the invention, assembled and with the jaws closed;

FIG. 16 is a perspective view of the instrument of FIG. 15;

FIG. 17 is a partly exploded view of the instrument of FIG. 15;

FIG. 18 is a side view of the lower portion of the frame of the instrument of FIG. 16, with the disposable loading unit received thereon;

FIG. 23 is a view taken from line 23—23 of FIG. 19, showing the lower part of the frame of the instrument;

FIG. 24 is a view taken from line 24—24 of FIG. 17, showing the upper part of the frame.

DETAILED DESCRIPTION OF THE PREFERRED EMBODIMENTS

Figure 3:
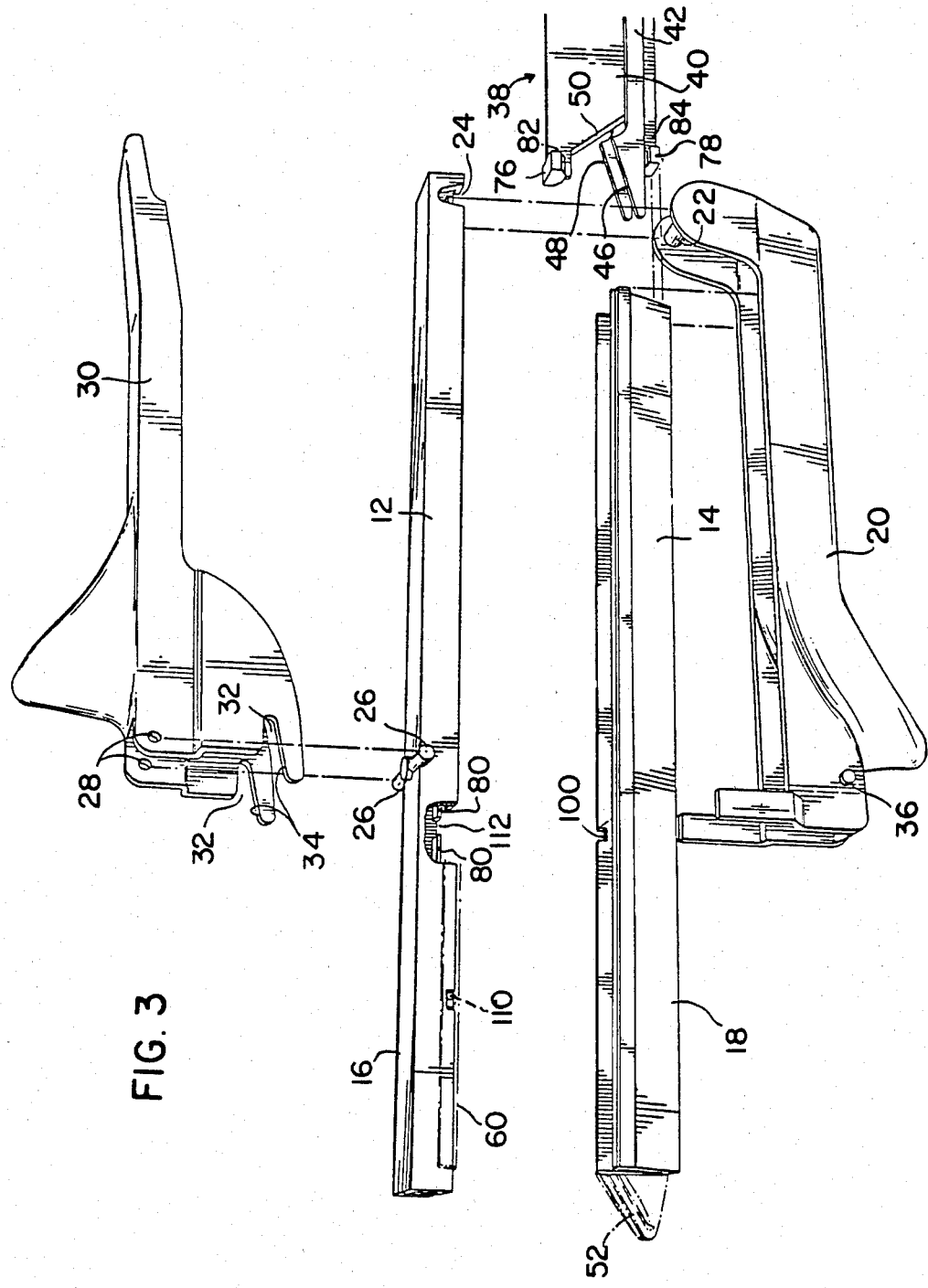
FIg. 3 is an exploded view of the instrument of FIG. 1.

In general construction and principle of operation, the illustrated embodiments of the instrument of the invention are similar to that described in U.S. Pat. No. 3,499,591, referred to above, the disclosure of which is incorporated herein by reference. Accordingly, the following description will only deal in detail with features of the instrument in regard to which it differs from that described in U.S. Pat. No. 3,499,591. For a fuller explanation of the principles and operation of the instrument, reference may be made to the above patent.

The first preferred embodiment 10 of the instrument of the invention includes an upper frame 12 and a lower frame 14. The forward end portion of upper frame 12 defines an elongate upper jaw 16, while the forward end portion of the lower frame 14 defines an elongate lower jaw 18. The portion of lower frame 14 rearward of jaw 18 fits into a channel-shaped handle member 20 having at its rear end a pivot bar 22 which is received in notches 24 at the rear end of upper frame 12. Intermediate its length, upper frame 12 has laterally projecting lugs 26 which fit in complementary openings 28 (see FIG. 3) defined in a bifurcated locking handle 30. The locking handle 30 has slots 32 defining camming surfaces 34 which cooperate with laterally projecting lugs 36 on handle member 20. By pivoting the locking handle 30 clockwise (as seen in FIG. 2) to cause camming surfaces 34 to slide on lugs 36, the locking handle 30 can be used to rotate the frames 12, 14 toward each other about the pivot bar 22 between the open condition shown in FIG. 2 and the closed condition shown in FIG. 1. The shape of the camming surfaces 34 is such as to lock the jaws 16, 18 together in the closed position.

The instrument 10 further includes a sliding pusher bar and knife assembly 38 comprising a central knife carrier 40 and laterally spaced pusher bars 42 and 44 located to either side of the knife carrier 40. The pusher bars 42, 44 terminate at their forward ends in slightly offset inclined pusher bar cams 46 and 48, respectively, and the knife carrier 40 includes an inclined knife 50 situated just to the rear of the pusher bar cams 46, 48.

Figure 11:
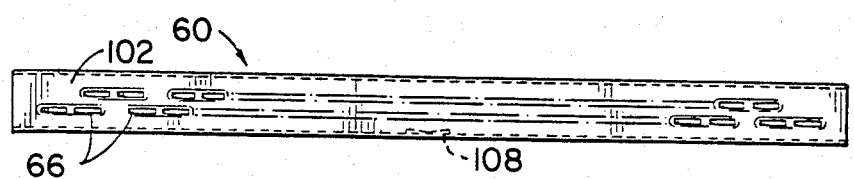
FIG. 11 is a top view of an elongate anvil member forming part of the instrument of FIG. 1.
Figure 12:
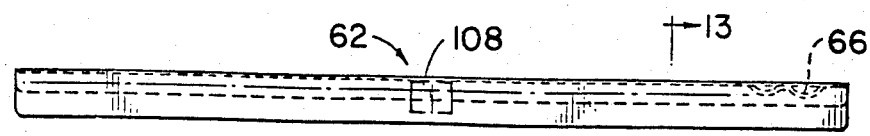
FIG. 12 is a side view of the anvil member of FIG. 11.
Figure 21:
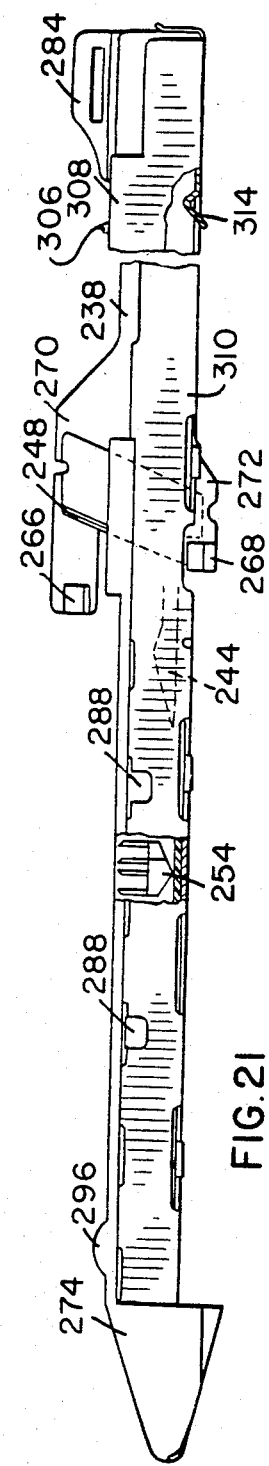
FIG. 21 is a side view of the disposable loading unit.
Figure 22:
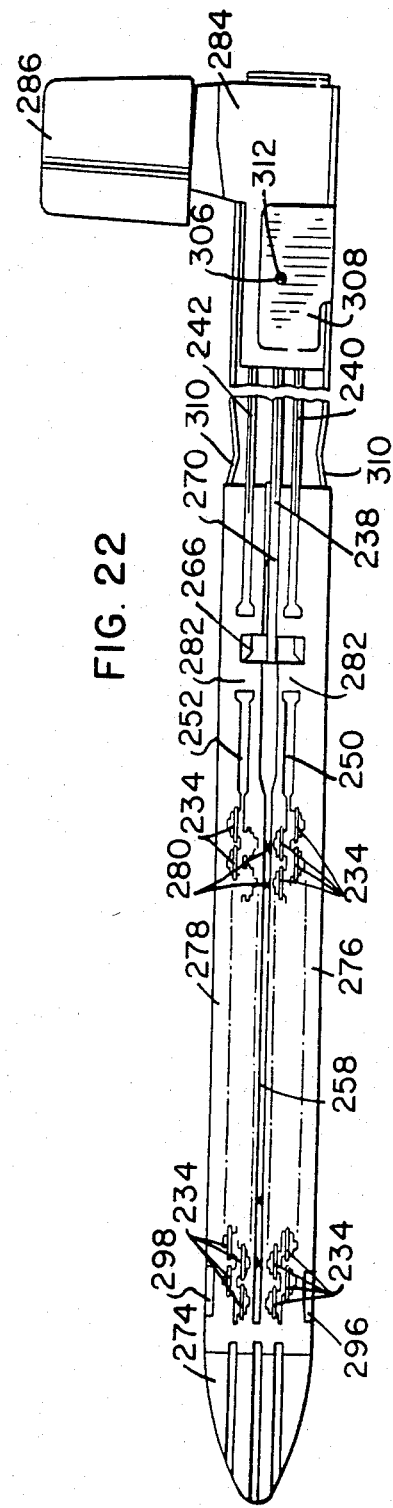
FIG. 22 is a top view of the disposable loading unit of FIG. 21.

For use, a disposable staple holder or magazine 52 (shown in phantom in FIG. 1 and in detail in FIGS. 8 and 9), comprising a body containing four laterally spaced longitudinal rows of staples, is inserted into a channel 54 defined in the upper surface of the lower jaw 18. The forward ends of the pusher bars 42, 44 are inserted into respective longitudinal slits 56 and 58 (see FIGS. 8 and 10) in the staple holder 52. Each slit 56, 58 accommodates a row of individual staple pushes (not shown in FIGS. 1-14, but identical to those shown in FIGS. 21 and 28). Two anvil members 60, 62 (shown in phantom in FIGS. 1 and 3, and in detail in FIGS. 11, 12 and 14) defining a longitudinal slot or space 64 between them, and having staple shaping depressions or buckets 66 in their outer surfaces complementary to the positions of the individual staples in the staple holder 52, are placed on the upper jaw 16.

The instrument 10 is inserted into a patient's body and manipulated so that the tissue to be cut and sutured is placed between the jaws 16 and 18, an incision to receive one of the jaws having previously been made in the tissue if necessary. The jaws 16, 18 are then closed and locked by means of locking handle 30 to grip the tissue firmly between the opposing staple holder 52 and anvil members 60, 62.

The pusher bar and knife assembly 38, which is initially in a rearward position (shown in FIG. 1) relative to the jaws 16 and 18, is then pushed forward by means of knob 68. The pusher bar cams 46, 48 cooperate with the camming surface of each individual staple pusher in turn to force the staples successively from the staple holder 62, through the gripped tissue and into engagement with the anvil depressions 66, which thereby, in cooperation with the cams 46 and 48, force the staples closed. Each slit 56, 58 contains one row of staple pushers each of which carries two mutually staggered rows of staples, so that in all, four staple rows are formed in the gripped tissue. The knife 50, which trails the pusher bar cams 46, 48 slightly and rides in central longitudinal slit 70 in the staple holder 52 and in space 64 between anvil members 60, 62, cuts the gripped tissue along a line between the two pairs of staple rows.

The ejection and closing of the staples generates forces tending to pry the jaws 16, 18 open, and also tending to separate the jaws 16, 18 laterally. If the stapler 10 is to be manufactured of relatively light-weight materials, it is necessary to provide additional support for the jaws 16, 18. To this end, each jaw 16, 18 is provided with support means, the preferred embodiment of which is described below.

To resist forces tending to open the jaws 16, 18 vertically during stapling, each jaw 16, 18 is provided with a longitudinal passageway 72 and 74, respectively, and the knife blade carrier 40, which is made of a rigid material, preferably metal, carries upper and lower laterally aligned shoes 76 and 78, respectively. Shoes 76, 78 ride in passageways 72, 74, respectively, in tandem with the pusher bar cams 46, 48 and provide the required local support to the jaws 16, 18 in the region of the pusher bar cams 46, 48 and knife blade 50 as these elements travel along the staple holder 52.

Figure 6:
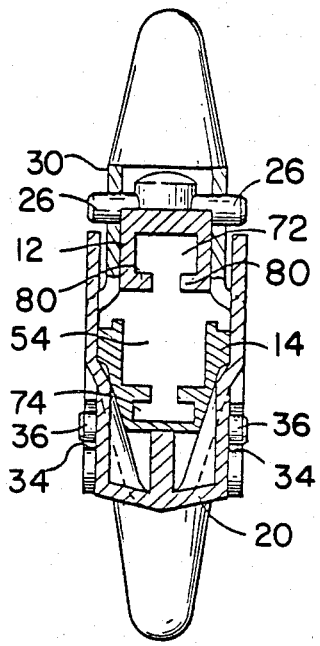
FIG. 6 is a sectional view taken from line 6—6 of FIG. 1.
Figure 7:
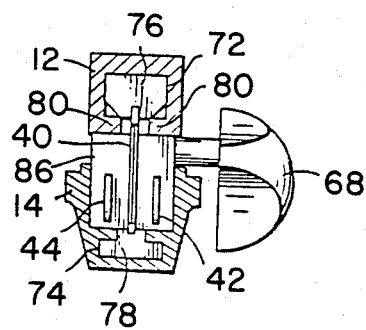
FIG. 7 is a sectional view taken from line 7—7 of FIG. 1, with parts of the instrument removed.
Figure 14:
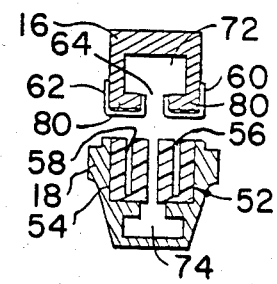
FIG. 14 is a sectional view taken from line 14—14 of FIG. 1.

As can be seen in FIGS. 6, 7 and 14, the longitudinal passageways 74 of the lower frame 14 is of generally T-shaped cross-section, the stem of the T extending into and communicating along its entire length with the channel 54. Upper frame 12 has inwardly directed longitudinally extending shoulders 80 for mounting the anvil members 60, 62, as will be described. The shoulders 80 and the rest of the upper frame 12 define longitudinally extending passageway 72 of generally T-shaped cross-section (if the portion of passageway 72 defined between shoulders 80 is ignored, the cross-section of the passageway 72 is rectangular).

The central knife carrier 40 (see particularly FIGS. 3, 4, and 5), as already stated, has an inclined knife 50 just to the rear of the pusher bar cams 46, 48 and includes upper and lower portions 82 and 84, projecting forward of and respectively extending above and below the pusher bars 46 and 48. On the projecting portions 82, 84 of the knife carrier 40 are upper and lower shoes 76 and 78, respectively. The vertical spacing between the shoes 76 and 78 is equal to the vertical spacing between the passageways 72 and 74 in the upper and lower frames 12 and 14 when the frames 12, 14 are locked together in the closed position (FIG. 1). The lower shoe 78 has a substantially T-shaped cross-section of the same shape and size as passageway 74, so that shoe 78 fits in passageway 74 with minimal clearance to allow substantially friction-free passage of the shoe 78 along the passageway 74. Similarly, upper shoe 76 fits in passageway 72 with minimal clearance to allow substantially friction-free passage.

The shoes 76 and 78 are located near the pusher bar cams 46 and 48 to provide support during stapling for the jaws 16 and 18 in the region of the cams 46, 48, substantially where the jaw-opening forces created by the stapling operation are greatest. Because the size and shape of shoes 76, 78 prevents the shoes 76, 78 from moving either laterally or vertically in their respective passageways 72 and 74, the shoes 76, 78 and passageways 72, 74 cooperate to resist both vertical opening and lateral misalignment of the jaws 16, 18 during stapling.

The rear ends of the pusher bars 42, 44 and of knife carrier 40 are mounted in a known manner in a suitable carrying block 86 to which operating knob 68 is secured.

The staple holder 52 (see FIGS. 8, 9 and 10) is generally similar to the known type described in the aforementioned U.S. Pat. No. 3,499,591 as to the number of staple rows and the design and location of the individual staple pushers. For a fuller description of these elements and the mannner in which the pusher bar cams 46, 48 cooperate with the individual staple pushers to eject the staples, reference may therefore be made to that patent.

Figure 8:
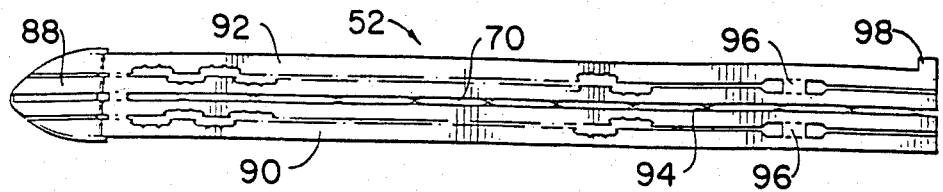
FIG. 8 is an underside view of a disposable staple holder adapted for use with the instrument of FIG. 1.
Figure 9:
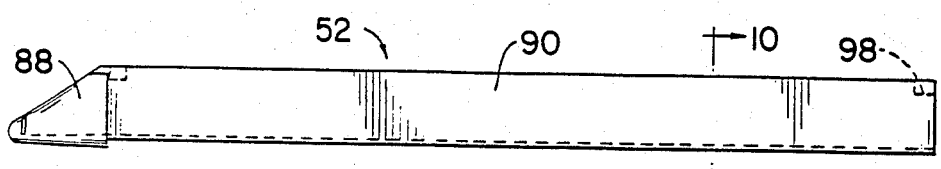
FIG. 9 is a side view of the cartridge of FIG. 8.
Figure 10:
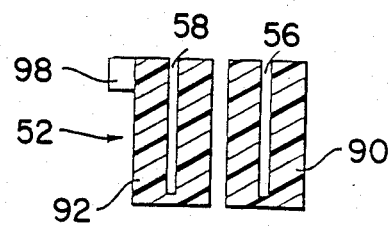
FIG. 10 is a sectional view taken from line 10—10 of FIG. 9.
Figure 13:
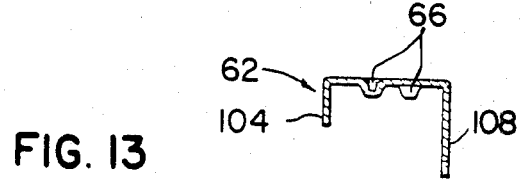
FIG. 13 is a sectional view taken from line 13—13 of FIG. 12.

As shown in FIGS. 8 and 9, the staple holder 52 comprises a solid nose portion 88 and a pair of longitudinal ribs 90 and 92 extending rearward from the nose portion 88 and defining slot 70 between them, which slot 70 extends through the entire thickness of the staple holder 52 to allow passage of the knife carrier 40. The inner, facing surfaces of the ribs 90 and 92 have bumps 94 to locate the knife carrier 40 laterally within slot 70. Longitudinal slits 56, 58 which accommodate the staple pushers and the staples are located in the ribs 90, 92, respectively. Friction pieces 96 are provided in slits 56, 58 to inhibit inadvertent forward motion of the pusher bars 42, 44.

In use, as indicated, the staple holder 52 sits in the channel 54 of the lower jaw 18 with the nose portion 88 projecting forward of the jaw 18 (see FIG. 1). The staple holder 52 is maintained in the correct longitudinal location by means of a projecting cartridge lug 98 received in a complementary cut-out 100 in one of the side walls of channel 54.

The significant difference between staple holder 52 and that described in U.S. Pat. No. 3,499,591 is that slot 70 extends all the way through the thickness of staple holder 52, to allow passage of the vertically extending knife carrier 40.

While the instrument 10 has been herein described as a reusable stapler used with a disposable, separate staple holder 52, it is also within the scope of the present invention for the staple holder 52 to be formed as an integral part of lower jaw 18, in which case the entire instrument 10 is disposed of after one use.

The anvil (see FIGS. 11, 12 and 13) comprises two like elongate anvil members 60, 62 which sit with a friction fit on the shoulders 80 of the upper jaw 16, as shown in FIG. 1, 3 and 14. When in place on jaw 16, the anvil members 60, 62 define a slit 64 between them to allow passage of the vertically extending knife carrier 40. Each anvil member 60, 62 comprises an anvil surface 102 with staple-shaping depressions or buckets 66, an inner wall 104 and an outer wall 106 that is longer, in a direction transverse to the anvil surface 102 than inner wall 104. The inner and outer walls 104, 106 are slightly tapered inward to provide the friction fit on shoulders 80. The outer walls 106 each have depressions 108 which are received in complementary depressions 110 in the side walls of the upper jaw 16 when the anvil members 60, 62 are in place at the proper longitudinal location on the upper jaw 16, with the staple shaping depressions 66 accurately aligned with the individual staples in staple holder 52.

While the instrument 10 as described includes two separate anvil members 60, 62 which fit on the shoulders 80 of upper jaw 16, it is also possible, particularly for a low-cost disposable instrument, to dispense with attachable anvils and to form the staple shaping depressions directly in the undersurfaces of shoulders 80 of the upper jaw 16.

The various components of the instrument 10 are assembled in the following manner (see particularly FIGS. 1 to 3). Initially, with a staple holder 52 correctly positioned in the channel 54 of lower jaw 20, the forward end of pusher bar and knife assembly 38 is inserted from the back into lower frame 14, with lower shoe 78 fitting in passageway 74, and the pusher bar and knife assembly 38 is moved forward along frame 14 until the pusher bars 42, 44 enter the longitudinal slits 56, 58 in ribs 90, 92 of staple holder 52 and are arrested by the friction pieces 96. (This position of pusher bar and knife assembly 38 relative to frame 14 is shown in FIGS. 1 and 2). Lower frame 14, with the pusher bar and knife assembly 38, is then fitted into handle member 20, suitable complementary locating means (not shown) being provided on the lower frame 14 and handle member 20 to align these elements longitudinally and to prevent relative movement of lower frame 14 and handle member 20 during staple ejection. Since the staples in staple holder 52 must be exactly aligned with the brackets 66 in anvil members 60, 62, the correct longitudinal position of frame 14 relative to handle member 20 must be maintained with great precision.

Anvil members 60, 62 are then fitted onto upper jaw 16, and lugs 26 of upper frame 12 are fitted into openings 28 of locking handle 30. Then with the locking handle 30 tilted upward, as shown in FIG. 2, notches 24 are engaged with pivot bar 22, completing the assembly of the instrument 10.

In use, the instrument 10 in the assembled, open condition, substantially as shown in FIG. 2, is inserted into a body cavity so that tissue to be stapled is accepted between jaws 16 and 18, and the instrument 10 is then locked by manipulation of locking handle 30 and cooperation of camming surfaces 34 with lugs 36. It will be noted that openings 112 (see FIG. 3) are provided in shoulders 80 of the upper frame 12 to allow upper shoe 76 to enter channel 72 as the jaws 16, 18 are closed. With tissue gripped between the jaws 16 and 18 and with the instrument 10 in the position shown in FIG. 1, the tissue is stapled and cut in the manner described in the aforementioned U.S. Pat. No. 3,499,591 by pushing forward on knob 68.

When stapling has been completed, the pusher bar and knife assembly 38 is retracted to the initial position, allowing upper shoe 76 to be removed from channel 72 through openings 112 as the locking handle 30 is rotated to open the instrument 10.

The shoes 76 and 78, received in passageways 72 and 74, clamp the jaws 16 and 18 securely together, resisting the jaw-opening forces that occur during stapling. The clamping effect of the shoes 76, 78 is provided at or immediately adjacent the portion of the jaws 16, 18 where the jaw-opening forces are greatest, i.e. where stapling is occurring. In addition, because the shoes 76, 78 are accurately aligned laterally with each other and are carried by a relatively rigid member, it will be appreciated that during stapling, as the shoes 76, 78 move along the passageways 72, 74 with minimal clearance, they also provide some degree of lateral support to the jaws 16, 18. As a result, the construction illustrated in FIGS. 1-14 particularly lends itself to manufacturing the jaws 16, 18 of relatively light weight disposable materials, although the construction is also suitable for use in instruments manufactured from heavier materials.

As shown in FIGS. 15-25, the second preferred embodiment 200 of the instrument of the invention includes an upper frame 202 and a lower frame 204. The forward end portion of the upper frame 202 defines an elongate upper jaw 206. The lower frame 204 comprises a tray 208 whose forward end portion defines an elongate lower jaw 210, and a handle member 212 whose upper surface is provided with a channel 214 (not shown) that receives the tray 208. The handle member 212 has at its rear end a pivot bar 216 which is received in a notch 218 at the rear end of upper frame member 202 (see FIG. 17). (The significant difference between a single notch 218 and two notches as in the embodiment of FIGS. 1–14 will be described below.) Pivot bar 216 also secures the rear end of tray 208 to the handle member 212. At an intermediate point along its length, the upper frame member 202 has laterally projecting lugs 220 which are pivotably received in complementary openings 222 formed in a bifurcated locking handle 224. The locking handle 224 can be used to open and close the jaws 206 and 210 about the pivot means 216, 218 between an open position (not shown, but analogous to that shown in FIG. 2) and the closed position shown in FIG. 15. To this end, locking handle 224 has slots 226 providing camming surfaces 228 which cooperate with laterally projecting lugs 230 on tray 208.

A disposable loading unit or cartridge 232, containing four longitudinal rows of staples 234 (see FIGS. 21, 22 and 25), is provided separately from the portions of the stapler 200 already described. The disposable loading unit (hereinafter referred to as a "DLU") 232 also includes a sliding pusher bar and knife assembly 236 comprising a central knife carrier 238 and laterally spaced pusher bars 240, 242 on either side of the knife carrier 238. The forward ends of the pusher bars 240, 242 terminate in inclined pusher bar cams 244, 246, (not shown) respectively, and the knife carrier 238 includes an inclined knife 248 located just to the rear of the pusher bar cams 244, 246. The DLU 232 has longitudinal slits 250, 252, each containing a row of individual staple pushers 254 and accommodating the pusher bar cams 244, 246. Each staple pusher 254 carries two staples 234, which are offset from each other laterally and longitudinally.

The underside of upper jaw 206 is provided with a plurality of staple forming depressions or brackets 256 for closing the staples 234 as the latter are ejected from the DLU 232 as described below. Alternatively, separate anvil members having brackets formed therein could be used, as in the embodiment of FIGS. 1–14.

Figure 19:
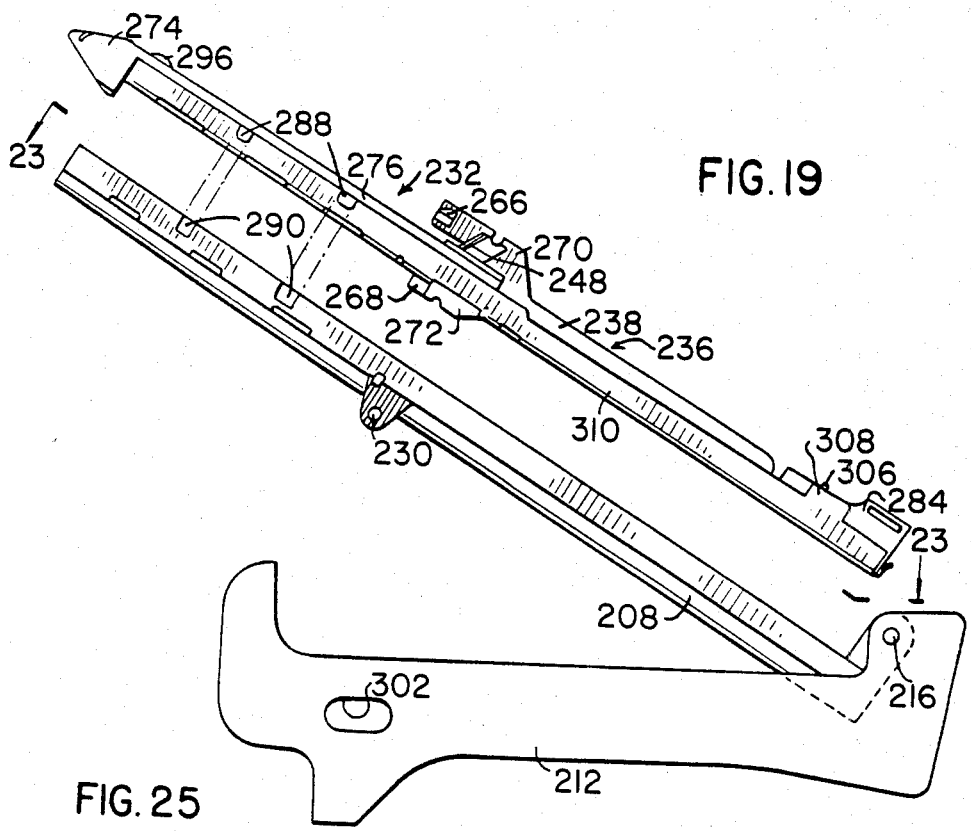
FIG. 19 is a view similar to FIG. 18, showing the manner of loading the disposable loading unit onto the lower part of the frame of the instrument.
Figure 25:
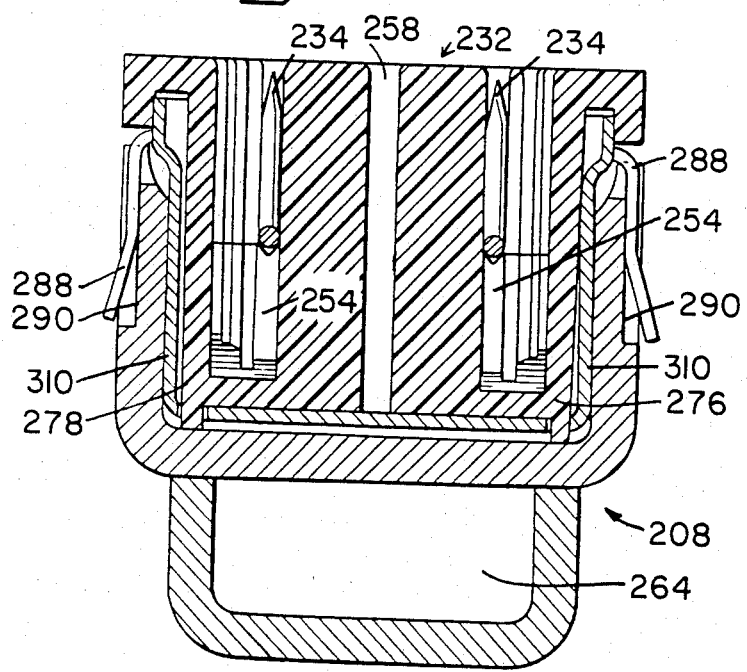
FIG. 25 is a sectional view taken from line 25—25 of FIG. 18.
Figure 20:
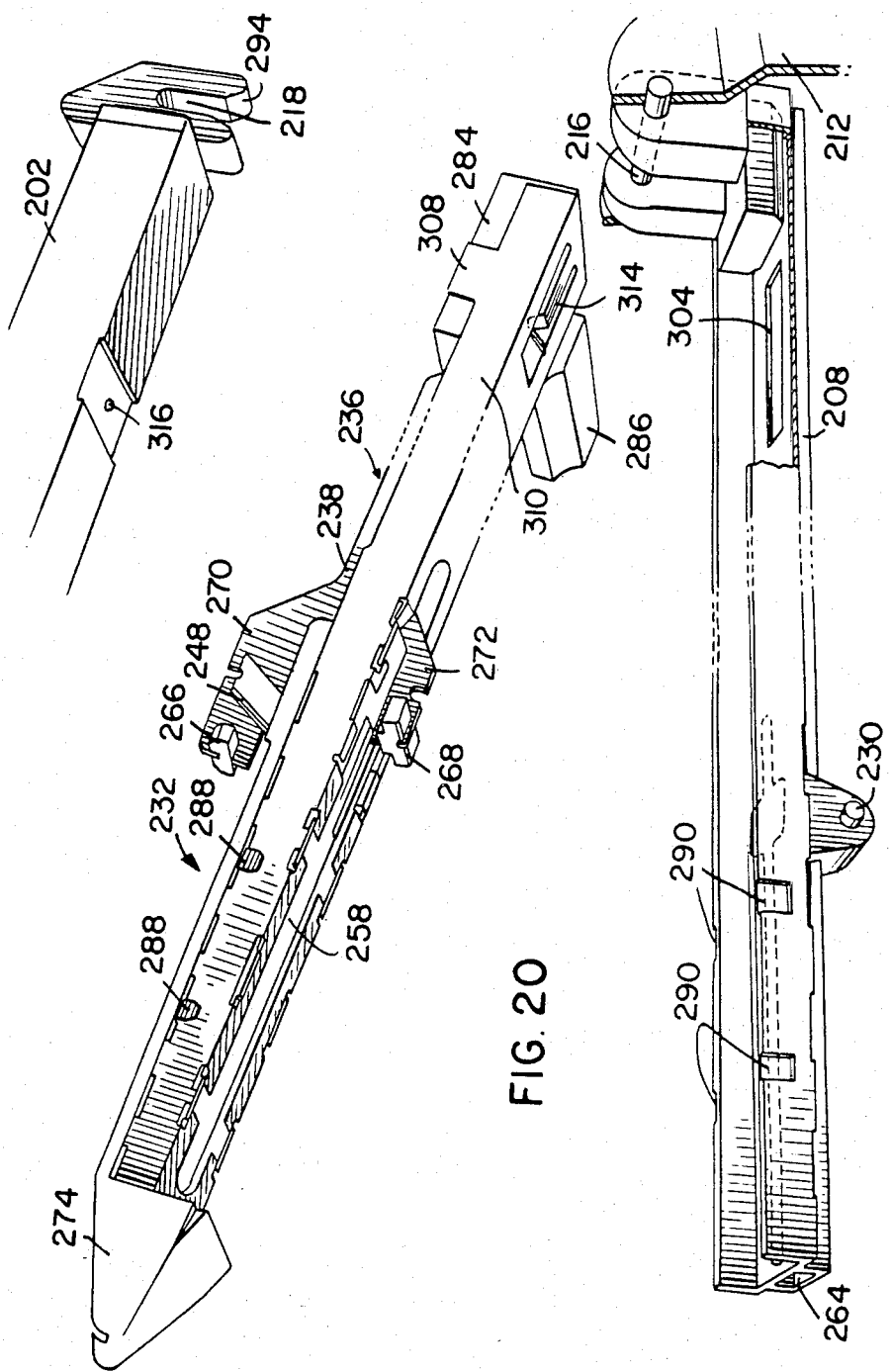
FIG. 20 is a view showing in more detail the manner of loading the disposable loading unit onto the frame.

For use, the DLU 232 is placed on the tray 208 of the lower frame 204 as indicated in FIG. 19 so that the staples 234 are aligned laterally and longitudinally with the individual buckets 256 on the underside of the upper jaw 206.

The instrument 220 is inserted into a patient's body and manipulated such that tissue to be cut and sutured is inserted between the jaws 206 and 210, an incision to receive one of the jaws having previously been made in the tissue if required. The jaws 206, 210 are then closed and locked by means of the locking handle 224 to grip the tissue firmly between the opposing DLU 232 and underside of upper jaw 206.

The pusher bar and knife assembly 236, which is initially in a rearward position relative to the jaws 206 and 210, is then pushed forward, causing the pusher bar cams 244 and 246 to move along the longitudinal slits 250 and 252, cooperating sequentially with camming surfaces on the individual staple pushers 254 to force each staple 234 in succession from the DLU 232, through the gripped tissue and into engagement with the anvil depressions 256, which thereby, in cooperation with the cams 244 and 246, close each staple 234. Each slit 250, 252 contains two mutually staggered rows of staples 234, so that four rows of staples 234 are formed in the gripped tissue. The knife 248, which trails the pusher bar cams 244, 246 slightly and rides in a central longitudinal slot 258 in the DLU 232 and in a slot 260 (not shown) defined in the underside of upper jaw 206 between the two pairs of rows of buckets 256, cuts the gripped tissue along a line between the two pairs of staple rows.

Each jaw 206, 210 is provided with a longitudinal passageway 262 and 264, respectively. The knife blade carrier 238, which is made of a rigid material, preferably metal, carries upper and lower laterally aligned shoes 266 and 268, respectively. Shoes 266 and 268 ride in passageways 262 and 264, respectively, in tandem with the pusher bar cams 244, 246 and provide the required local support to the jaws 206, 210 in the region of the pusher bar cams 244, 246 and knife blade 248 as these elements travel along the jaws 206, 210 during operation of the stapler 200.

The central knife carrier 238, as indicated, carries an inclined knife 248 just to the rear of the pusher bar cams 244, 246 and includes upper and lower portions 270, 272 projecting forward of and respectively extending above and below the pusher bars 240, 242. On the upper and lower projection portions 270, 272 of the knife carrier 238 are disposed the upper and lower shoes 266 and 268, respectively. The vertical spacing between the shoes 266 and 268 is equal to the vertical spacing between the passageways 262 and 264 when the frames 206, 210 are locked together in the closed position. The lower shoe 268 has a substantially T-shaped cross-section and is so dimensioned as to fit in passageway 264 with minimal clearance to allow substantially friction-free passage of the shoe 268 along the passageway 264. Similarly, upper shoe 266 is shaped to fit in passageway 262 with minimal clearance to allow substantially friction-free passage. The shoes 266, 268 cooperate with passageways 262, 264 in the same way and have the same effect as in the embodiment of FIGS. 1–14.

The DLU 232, as shown in FIGS. 19–22, is generally similar to the staple holder described in the aforementioned U.S. Pat. No. 3,499,591 insofar as the number of staple rows and the design and location of the individual staple pushers 254 are concerned. In the present case, the DLU 232 comprises a solid nose portion 274 and a pair of longitudinal ribs 276 and 278 extending rearward from the nose portion 274 and defining therebetween slot 258, which extends through the entire thickness of the DLU 232 and accommodates the upper projecting portion 270 of the knife carrier 238. The inner facing surfaces of the ribs 276 and 278 have bumps 280, and friction pieces 282 are provided in slits 250, 252. At the rear end of pusher bar and knife assembly 236, the pusher bars 240, 242 and knife carrier 238 are mounted in a known manner in a suitable carrying block 284, which is an integral part of DLU 232 and has an operating knob 286 or the like. The forward ends of the pusher bars 240, 242 are accommodated in the longitudinal slits 250, 252 of the DLU 232, which permanently engage the pusher bar cams 244, 246, respectively.

In use, as indicated, the DLU 232 sits in the tray 208 of the lower frame 204 with the nose portion 274 of the DLU 232 projecting forward of the end of the jaw 210. Projecting cartridge lugs 288 and complementary cutouts 290 in one of the side walls of lower jaw 210 retain the DLU 232 in the proper longitudinal position relative to the tray 208.

By making the staple magazine and the pusher bar and knife assembly as a single unit, the assembly of the stapler 200 is facilitated. Instead of attaching the staple magazine to the stapler frame, then inserting the pusher bars into the magazine to engage the pusher bar cams and adjusting the pusher bar and knife assembly to ensure that it is properly aligned, the DLU 232 of the invention can be loaded into the stapler 200 in a single step. This makes assembly of the stapler 200 significantly quicker, easier and more reliable than has previously been possible. For example, the risk of cutting oneself in attempting to insert the pusher bars into the staple magazine is eliminated.

As already stated, the anvil means (see FIG. 24) comprises a plurality of like individual buckets 256 defined in the underside of the upper jaw 206. A slot 260 is provided between the rows of buckets 256 to allow passage for the upper extending portion 270 of knife carrier 238.

In order for the stapler 200 of the invention to function properly, it is necessary that the anvil buckets 256 be aligned as precisely as possible both laterally and longitudinally with the staples 234 in the DLU 232. Although the first preferred embodiment 10 of the invention is shown with notches 24 formed in the side walls of the upper frame 12 to cooperate with pivot bar 22, it has been found advantageous for longitudinal alignment to replace that structure with the one shown in the second preferred embodiment 200 (see FIGS. 17 and 20). In the latter embodiment 200, a trunnion block 294 is located at the rear end of upper frame 202. A single deep notch 218 is provided in the underside of trunnion block 294 for pivotal engagement with pivot bar 216. It has been found that this structure eliminates longitudinal misalignment of the anvil buckets 256 and staples 234.

For good lateral alignment, two conditions must be satisfied. First, the longitudinal axis of jaw 206 must be exactly parallel to and directly above that of the DLU 232. Second, lateral flexing of the jaws 206, 210 under the large loads that occur during stapling must not be allowed to misalign the anvil buckets 256 and staples 234. The first condition is satified by careful manufacture of the stapler 200. The second is satisfied by means of lugs or tabs 296, 298 located on each side of the distal end of jaw 210. Tabs 296, 298 extend parallel to each other toward jaw 206 and are positioned to engage the sides of jaw 206 when the jaws 206, 210 are closed, if no tissue is present between the distal ends of the jaws 206, 210. If tissue does block such engagement, the tabs 296, 298 tend to press the tissue slightly around jaw 206, thereby clamping the tissue more firmly in place than if the tabs 296, 298 were absent and clamping jaw 206 to prevent lateral movement thereof relative to jaw 210. In this manner, proper lateral alignment is ensured.

The various components of the instrument 200 are assembled in the following manner. Initially, a DLU 232 is positioned on the tray 208 of lower fram 204 as shown in FIGS. 18 and 19. Tray 208, carrying the DLU 232, is then rotated about pivot bar 216 until the tray 208 lies flat on the upper surface of the handle member 212, in which position the tray 208 is retained by the engagement of laterally extending lugs 230 in apertures 302 provided in the handle member 212. Notch 218 is then engaged with pivot bar 216 to complete the assembly of the instrument 200.

In use, the assembled instrument 200 in the jaws-open position is inserted into a body cavity so that the tissue to be stapled is accepted between jaws 206 and 210. The jaws 206, 210 of the instrument 200 are then closed and locked by manipulation of locking handle 224 and cooperation of camming surfaces 228 with lugs 230. Openings 304 (see FIG. 24) are provided in the upper frame 202 which allow upper shoe 266 to enter channel 262 as the jaws 206, 210 are closed. With tissue gripped between the jaws 206, 210 and the instrument 200 in the closed condition shown in FIG. 15, knob 286 is pushed forward to effect stapling in the manner described in U.S. Pat. No. 3,499,591.

When stapling is completed, the knob 286 is retracted to the initial position, allowing shoe 266 to be removed from channel 262 through openings 304, so that the instrument 200 can be opened and removed from the body cavity.

It is possible to move the pusher bar and knife assembly 236 forward from its initial rearward position accidentally, before the jaws 206, 210 have been locked closed on the tissue to be stapled. If this occurs, some or all of the staples 234 may be ejected from the DLU 232 and wasted, since they cannot suture the tissue in the proper manner unless the tissue is firmly gripped between the jaws 206, 210 while the jaws 206, 210 are locked.

The use of friction pieces 282 to solve this problem is known; another solution is also now disclosed, as one aspect of the present invention.

The stapler 200 of the invention is provided with a detent mechanism to prevent accidental operation. The detent mechanism comprises first and second detent elements which cooperate to lock the pusher bar and knife assembly 236 into its initial, rearward position, and a release mechanism that unlocks the pusher bar and knife assembly 236 for longitudinal motion when the jaws 206, 210 are locked closed.

In the preferred embodiment 200 shown in FIGS. 15-25, the first detent element is a peg 306 on the upper surface of carrying block 284, and the second detent element is a tab 308 of metal integral with a metal strip 310 that defines a trough containing and secured to the ribs 276, 278 and slidably receiving the carrying block 284. The tab 308 is folded over the upper surface of the carrying block 284 with a slight clearance between them and has an aperture 312 to receive the peg 306. A portion of the bottom of the trough is formed into a leaf spring 314 that urges the peg 306 into aperture 312, locking the pusher bar and knife assembly 236 in its rearward position.

The release mechanism comprises a second peg 316 on the underside of upper frame 202 and so located that when the stapler 200 is assembled and the jaws 206, 210 are closed, the second peg 316 depresses peg 306, against the force of the spring 314, a sufficient distance to disengage peg 306 and aperture 312, allowing the pusher bar and knife assembly 236 to move forward when a forward force is applied to operating knob 286.

While only two preferred embodiments of the invention have been described in detail, the invention is not limited to the specific features described, and many modifications that will now be apparent to those skilled in the art are possible within the scope of the appended claims. Thus, while the invention has been particularly described in relation to surgical stapling, the invention is not limited to this application, but may also be applied to other fastening instruments having opposed jaws which require stabilization while fastening means are applied to matter gripped between the jaws. For example, the invention may be applied to instruments for applying certain types of surgical clips or to instruments for applying surgical fastening devices of the type set out in U.S. Pat. No. 4,060,089. In addition, any of the features of the invention described in connection with the embodiment of FIGS. 15-25 can be used in the embodiment of FIGS. 1-14, if desired. Accordingly, the scope of the invention is to be limited not by details of the preferred embodiments described herein, but only by the appended claims.

What is claimed is:

1. A disposable loading unit for use with a surgical stapler of the type having a first jaw adapted to carry a disposable loading unit, and using a pusher bar to eject staples sequentially from a disposable loading unit carried on the first jaw, and having a second jaw facing the first jaw for closing staples ejected from a disposable loading unit on the first jaw;

said disposable loading unit comprising: a body containing at least one longitudinally extending row of surgical staples and having a first longitudinal passage for receiving a pusher bar; camming means for cooperating with a pusher bar to eject said surgical staples from said body; and a slot extending through the entire thickness of said body for receiving jaw support means for supporting the stapler jaws; further comprising jaw support means for supporting the stapler jaws, wherein said jaw support means comprises shoe means slidably movable along said slot in tandem with a pusher bar when a pusher bar is received in said first longitudinal passage, said shoe means being adapted to cooperate with a surgical stapler of said type for maintaining the jaws of the surgical stapler substantially stationary relative to each other in the vicinity of said shoe means.

2. The disposable loading unit of claim 1, wherein said shoe means comprises upper and lower shoes rigidly connected to each other.

3. The disposable loading unit of claim 1, further comprising pusher bar means received in said longitudinal passage for expelling staples from said body sequentially, said pusher bar means being movable in tandem with said shoe means.

4. The disposable loading unit of claim 3, further comprising knife means received in said slot and movable with said pusher bar means for cutting tissue after it has been stapled with staples ejected from said disposable loading unit, said knife means being movable in tandem with said pusher bar means.

* * * * *